(12) United States Patent
Shi et al.

(10) Patent No.: US 10,131,916 B2
(45) Date of Patent: *Nov. 20, 2018

(54) REGULATORY ELEMENT FOR HETEROLOGOUS PROTEIN PRODUCTION IN THE FRUITING BODY OF FILAMENTOUS FUNGI

(71) Applicant: Intrexon Corporation, Blacksburg, VA (US)

(72) Inventors: Zhixin Shi, Cary, NC (US); Jack Q. Wilkinson, Cary, NC (US); Donald S. Walters, Chapel Hill, NC (US); C. Peter Romaine, State College, PA (US)

(73) Assignee: Intrexon Corporation, Blacksburg, VA (US)

( * ) Notice: Subject to any disclaimer, the term of this patent is extended or adjusted under 35 U.S.C. 154(b) by 124 days.

This patent is subject to a terminal disclaimer.

(21) Appl. No.: 14/851,819

(22) Filed: Sep. 11, 2015

(65) Prior Publication Data

US 2017/0073693 A1  Mar. 16, 2017
US 2018/0073032 A9  Mar. 15, 2018

Related U.S. Application Data

(63) Continuation of application No. 13/819,356, filed as application No. PCT/US2011/049741 on Aug. 30, 2011, now Pat. No. 9,145,561.

(60) Provisional application No. 61/460,767, filed on Aug. 30, 2010.

(51) Int. Cl.
*C12N 15/63* (2006.01)
*C12N 15/80* (2006.01)

(52) U.S. Cl.
CPC .................................. *C12N 15/80* (2013.01)

(58) Field of Classification Search
CPC ........................................................ C12N 15/80
USPC ........................................................ 536/24.1
See application file for complete search history.

(56) References Cited

U.S. PATENT DOCUMENTS

| 6,812,339 B1 | 11/2004 | Venter et al. | |
| 9,145,561 B2* | 9/2015 | Shi | C07K 14/8117 |
| 2007/0014817 A1 | 1/2007 | Barale et al. | |
| 2013/0219554 A1* | 8/2013 | Shi | C07K 14/8117 800/278 |

FOREIGN PATENT DOCUMENTS

WO   2012030827 A1   3/2012

OTHER PUBLICATIONS

NCBI, GenBank submission AC092373, 39 pages, last accessed on Feb. 6, 2015.

* cited by examiner

*Primary Examiner* — Li Zheng
(74) *Attorney, Agent, or Firm* — McKee, Voorhees & Sease, PLC

(57) ABSTRACT

The present invention provides compositions and methods for regulating expression of nucleotide sequences in fungi. Compositions are novel nucleotide sequences for a tissue preferred promoter isolated from the *Agaricus bisporus* lectin gene. The sequences drive expression preferentially to fruit body tissue. A method for expressing a nucleotide sequence in fungi using the regulatory sequences disclosed herein is provided. The method comprises transforming a fungal cell to comprise a nucleotide sequence operably linked to one or more of the regulatory sequences of the present invention and regenerating a stably transformed fungus from the transformed cell.

13 Claims, 4 Drawing Sheets

Specification includes a Sequence Listing.

GATCTGAACACGCGTCGTTTACCTCCGGGGTGAGTCTCCTGGCACCTTGACAGAATCTAGAATACGATGATCG
pAGN-750→
CACCCTCGATTCCCATGAGCTAAAAATATCTGGTCCTGGCACTAGTCACAGTGGTCACCGACTCGAAAATTTC
                                pAGN-1279 →
CCCGTCCATAGTTAACTTTTTTCAACCACAAGTACTCAATCAAATCTACTAGCTTGTAGAAACATTGTAGCGCTT
                                                                                      pAGN-1280 →
GATGCTGAATAAATTCAATGCAATCATATAGCATACTACAGATCAACAGGTGCTCAAGCTCAAGCGGGACACTC

GATCTATAATTAGCACATACCCCAAAGTGCGGGGGTTAATGGCGCTGGACACTTCGTCTTCATAGATATGGCCA
    pAGN-1281 →                                                                                    pAGN-1282 →
AGCATCCTTCATGCCATGCTCGAATTATGCTACTTGTAGATAAGTTTATCTACACCCGCACGGACCAACTAACGT
                                       pAGN-1283 →
AGATATATAACGATGTCCGATACTTGTGAATACCTCAGTGGATTATATCCTCTTGACTGCGATTCACCTGCTCCA
pAGN-1304 →                                                                                          pAGN-1305→
CTAACACAGTAACCATCTTTCTCTACCACTGTTTCAACTAACTCATAACGTTGAGCAGACCATG (SEQ ID NO: 1)

*FIG. 6*

Deletion analysis for Lectin promoter

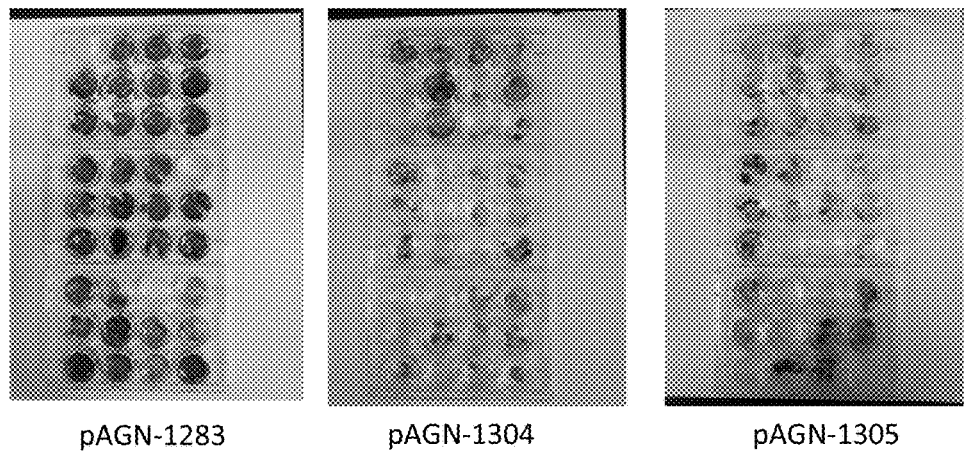

pAGN-1283            pAGN-1304            pAGN-1305

*FIG. 7*

REGULATORY ELEMENT FOR HETEROLOGOUS PROTEIN PRODUCTION IN THE FRUITING BODY OF FILAMENTOUS FUNGI

CROSS-REFERENCE TO RELATED APPLICATIONS

This application claims priority and is related to U.S. Provisional Application Ser. No. 61/460,767, filed on Aug. 30, 2010 and entitled REGULATORY ELEMENT FOR HETEROLOGOUS PROTEIN PRODUCTION IN THE FRUITING BODY OF FILIMENTOUS FUNGI. The entire contents of this patent application are hereby expressly incorporated herein by reference including, without limitation, the specification, claims, and abstract, as well as any figures, tables, or drawings thereof.

This application is also related to U.S. patent application Ser. No. 13/819,356, now U.S. Pat. No. 9,145,561, which is the National Phase application claiming priority to PCT/US11/049741 filed Aug. 20, 2011 and entitled REGULARTORY ELEMENT FOR HERETLOGOUS PROTEIN PRODUCTION IN THE FRUITING BODY OF FILAMENTOUS FUNGI. The entire contents of this patent application are hereby expressly incorporated herein by reference including, without limitation, the specification, claims, and abstract, as well as any figures, tables, or drawings thereof.

FIELD OF THE INVENTION

The present invention relates to the field of molecular biology, more particularly to regulation of gene expression in fungi. The novel compositions and methods can be used to improve fungal species by recombinant technologies known to those of skill in the art, such as the improved pathogen, pest, and pesticide resistance, yield quantity and quality, extended produce shelf life, improved culinary, nutritional, and medicinal value, and the like, as well as the commercial production of heterologous proteins.

BACKGROUND OF THE INVENTION

About 40% of the commercially available enzymes are derived from filamentous fungi. Lowe, Handbook of Applied Mycology. Fungal Biotechnology (eds.) Arora, D. K. Elander, R. P. & Mukerji, K. G. 681-708 (Marcel Dekker, New York; 1992). These enzymes are usually produced by species of the genera *Aspergillus* and *Trichoderma*. Because they secrete large amounts of protein into the medium, they can be grown in large-scale fermentation, and they are generally accepted as safe for the food industry.

General problems associated with the commercial cultivation of mushrooms (*Agaricus bisporus*) include diseases caused by pathogens like *Verticillium fungicola* (dry bubble), *Trichoderma aggressivum* (green mold), *Pseudomonas tolaasii* (blotch), and dsRNA viruses (La France disease and patch disease), the major insect pest [sciarid fly (*Lycoriella mali*)], an extremely short shelf life of the product related to bacterial spoilage and rapid senescence, and browning (bruising) of the fruit body associated with the action of endogenous poly-phenoloxidases (PPO, like tyrosinase). To further improve product quality, conventional breeding programs for *A. bisporus* have been only moderately successful and may not be sufficient in the long term. This is because conventional breeding techniques for fungi are highly time consuming, and because the genetic variation in commercially available strains is limited, offering little advancement by selection (Horgen et al. "Homology between mitochondrial DNA of *A. bisporus* and an internal portion of a linear mitochondrial plasmid of *Agaricus bitorquis*" Curr Genet. 1991. 19:495-502).

In the case of *A. bisporus*, the main obstacle to effective breeding strategies is the rather abnormal life cycle involving the unusual simultaneous segregation of either parental nucleus into one basidiospore. After outgrowth of this basidiospore, heterokaryotic mycelium is formed containing nuclei and genetic characteristics that do not differ from those present in the parental mycelium. In addition, only little recombinational activity is observed during meiosis (Summerbell et al. Genetics, October 123(2) 1989 pp. 293-300).

To overcome the limitations of conventional breeding, investigators all over the world have attempted to develop and improve transformation methods for commercial mushrooms, such as *A. bisporus*, for the introduction of novel characteristics. For other fungi, as well as plants, animals, and bacteria, the application of gene transfer technology is quite common and has already resulted in commercial application.

In order to enhance the economies of protein production in microorganisms, such as fungi, there have been substantial efforts to improve the efficiency of transcription and translation, maximize the proportion of total protein directed to production of the desired product, enhance the viability of the modified host, and improve the efficiency with which the modified host may be obtained. The primary promoter used in fungal transformation to date is the glyceraldehyde-3-phosphate dehydrogenase (gpd) promoter. Using strong promoters to express heterologous genes in appropriate hosts is a major strategy in biotechnological applications. The gpd promoter is a strong promoter that can be induced by any carbon source and has been widely used in the expression of heterologous proteins in *Saccharomyces cerevisiae*, *Pichia pastoris* and other yeasts.

The gpd genes have also been cloned from basidiomycetous fungi, including *Schizophyllum commune*, *Phanerochaete chrysosporium*, *Agaricus bisporus* (Harmsen et al., 1992), and *Lentinula edodes* (Hirano et al., 1999). Among these mushrooms, genetic transformation using homologous gpd promoter was reported to be successful only in *A. bisporus*, *Flammulina velutipes* and *L. edodes* (Hirano et al., 2000, Kuo et al., 2004, van de Rhee et al., 1996). Although heterologous promoters have been used for the expression of drug-resistant marker genes, the genetic transformation is not sufficient to express heterologous genes (Ruiz-Diez, 2002). To sufficiently and effectively express a heterologous gene, it is important for a host cell to recognize the promoter sequence by its transcriptional machinery. Chun-Yi Kuo et al. demonstrated that a heterologous gene, hygromycin B phosphotransferase gene (hpt), can be expressed in *F. velutipes* (Kuo et al., 2004). However, it was found that although the gpd genes in basidiomycetous fungi are highly similar, these gene differ significantly in their promoter regions.

As illustrated by the foregoing, there is a continuing need in the art for development of effective, convenient, and expeditious fungal transformation systems and gene expression components.

It is thus an object of the present invention to provide a transformation system and in particular a strong regulatory element for fungi that will accomplish the foregoing need.

A further object of this invention is to provide mechanisms for application of transgenic techniques such as those applied to bacteria, non-filamentous fungi (yeast), plants, and animals to increase yield, disease, and pest resistance, product quality, shelf life, or culinary, nutritional, or medicinal value, to produce heterologous proteins commercially, or other such protocols.

It is yet another object of the invention to provide regulatory elements capable of driving high level protein accumulation of operably linked sequences in the fruit body of fungi, as well as tissues in plant, or animal cells.

It is yet another object of the invention to provide regulatory elements polynucleotide constructs, vectors, and transformed cells for use in such transgenic protocols.

Other objects of the invention will become apparent from the description of the invention that follows.

SUMMARY OF THE INVENTION

The invention comprises an isolated regulatory element/promoter comprising a polynucleotide sequence selected from the group consisting of a) a polynucleotide sequence comprising the nucleic acid sequence as shown in SEQ ID NO:1, SEQ ID NO:2, SEQ ID NO:3 or SEQ ID NO:4; and b) a fragment of the polynucleotide sequence of a) capable of regulating transcription of an operably linked polynucleotide molecule in a fungal cell.

The invention also comprises a polynucleotide construct comprising the promoter of the invention operably linked to a heterologous polynucleotide molecule.

The invention also includes a transformed cell comprising the construct of the invention as well as methods of transformation using the constructs of the invention and heterologous protein products produced thereby.

The invention is directed to a promoter from an *A. bisporus* lectin-encoding gene, useful as a regulatory region and providing for expression of a nucleotide sequence of interest. In an embodiment, the accumulation of a heterologus protein or nucleotide sequence of interest is driven to the fruit body tissue. The invention is further directed to functional fragments that drive expression of a heterologus protein or nucleotide sequence of interest—in the fruit body tissue. Expression cassettes that incorporate the promoter driving expression of a nucleotide sequence, plants, fungi or bacterial cells expressing same, and methods of use in modulating expression of nucleotides sequences are within the scope of the invention.

DESCRIPTION OF FIGURES

FIG. 6 depicts the sequences of the lectin promoter (SEQ ID NO: 1). 5' end DNA sequences in each vector are underlined and the corresponding vector identified. All vectors share the same 3' sequence as presented. pAGN-755 and pAGN-750 share the identical sequence.

FIG. 7 shows the GUS staining of liquid mycelium culture of the events generated from truncated promoters shown in Table 5.

DETAILED DESCRIPTION OF THE INVENTION

Figure 1:
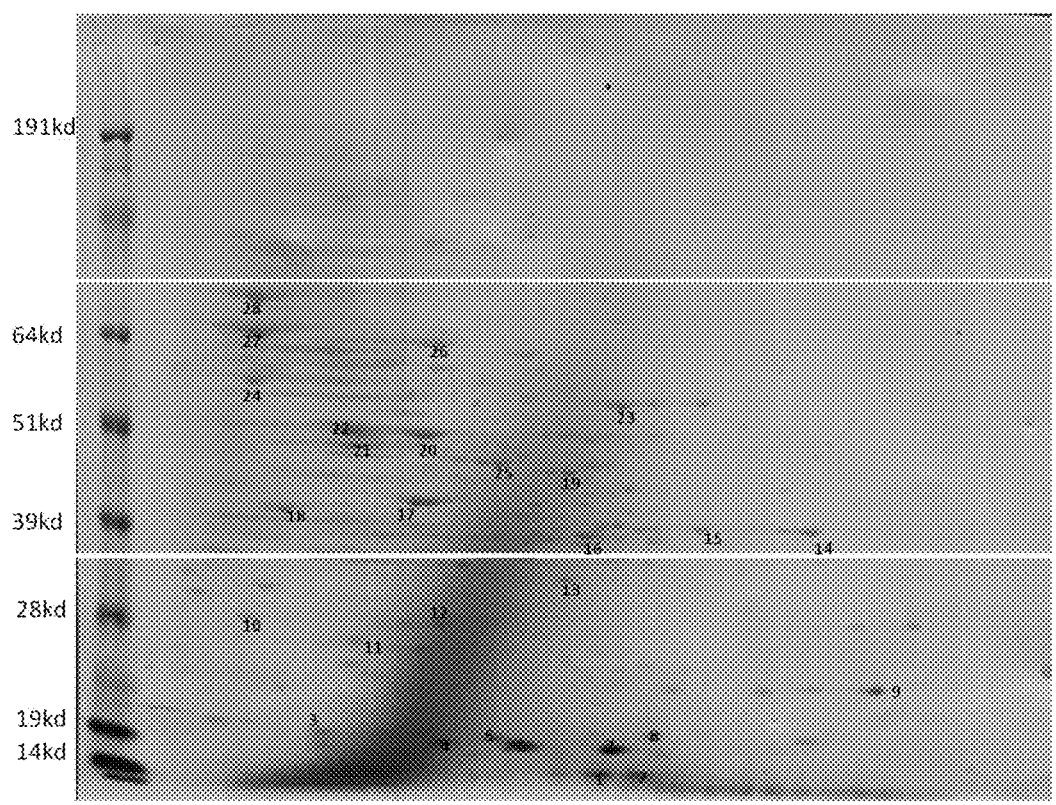
FIG. 1 is a 2-D gel analysis of proteins extracted from *Agaricus bisporus* fruiting bodies. Protein separation on 2-D SDS PAGE was performed according to the manufacturer's recommendation using IPG drystrips for the first dimension isoelectric focusing, and NuPAGE pre-cast gel system from Invitrogen for the 2nd dimension separation. The numbers identify protein spots excised for MS and MS/MS analysis.

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

In accordance with the invention, nucleotide sequences are provided that allow regulation of transcription and accumulation of the cognate protein or nucleotide sequence of interest in fruiting body tissue. Thus, the compositions of the present invention comprise novel nucleotide sequences for fungal regulatory elements natively associated with the nucleotide sequences coding for *A. bisporus* lectin protein.

In an embodiment, the regulatory element drives transcription in a fungal tissue or more specifically achieves expression of a protein or transcript of interest in a fungal fruiting body tissue, wherein said regulatory element comprises a nucleotide sequence selected from the group consisting of: a) sequences natively associated with, and that regulate expression of DNA coding for lectin protein); b) the sequence of SEQ ID NO: 1, SEQ ID NO:2, SEQ ID NO:3 or SEQ ID NO:4; or c) a sequence comprising a functional fragment of the nucleotide sequence set forth in SEQ ID NO:1, SEQ ID NO:2, SEQ ID NO:3 or SEQ ID NO:4.

Further embodiments are to expression cassettes, transformation vectors, fungi, bacteria, and bacterial and fungal cells comprising the above nucleotide sequences. The invention is further to methods of using the sequence in plants, fungi, and bacterial tissues and their cells.

A method for expressing an isolated nucleotide sequence in a fungus using the regulatory sequences disclosed herein is provided. The method comprises transforming a fungal cell with a transformation vector that comprises an isolated nucleotide sequence operably linked to one or more of the regulatory sequences of the present invention and regenerating a stably transformed fungus from the transformed fungal cell. In this manner, the regulatory sequences are useful for controlling the expression of endogenous as well as exogenous products in a fruiting body tissue.

Alternatively, it might be desirable to inhibit expression of a native DNA sequence within the tissues of a fungus to achieve a desired phenotype. In this case, such inhibition might be accomplished, for example, with transformation of a fungus to comprise the promoter operably linked to an antisense nucleotide sequence, hairpin, RNA interfering or other nucleic acid molecule, such that expression of the molecule interferes with translation of the mRNA of the native DNA sequence or otherwise inhibits expression of same in a subset of the cells of the fungus.

Under the regulation of the regulatory element will be a sequence of interest, which will provide for modification of the phenotype of a fungus. Such modification includes modulating the production of an endogenous product, as to amount, relative distribution, or the like, or production of an exogenous expression product to provide for a novel function or product in a fungus. Such a promoter is useful for a variety of applications, such as production of transgenic fungi with desired traits, including, for example, altered content, protein quality, cell growth or nutrient quality or preferably for the production of heterologous proteins.

By "fruiting body tissue" promoter is intended expression that is capable of transcribing an operatively linked nucleotide sequence efficiently and thereby achieving accumulation of a protein or nucleotide sequence of interest at high levels in the described tissues, here the fruiting body tissue cells. Tissue can refer to a cell of a particular tissue.

By "regulatory element" is intended sequences responsible for expression of the linked nucleic acid molecule including, but not limited to, promoters, terminators, enhancers, introns, and the like.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements that impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region. Thus the promoter region disclosed here may comprise upstream regulatory elements such as those responsible for tissue and temporal expression of the nucleic acid molecule, and may include enhancers, the DNA response element for a transcriptional regulatory protein, ribosomal binding sites, transcriptional start and stop sequences, translational start and stop sequences, activator sequence and the like.

In the same manner, the promoter elements that enable such expression can be identified, isolated, and used with other core promoters to confirm expression in fruiting body tissue. By core promoter is meant the minimal sequence required to initiate transcription, such as the sequence called the TATA box, which is common to promoters in genes encoding proteins. Thus the upstream promoter of SB-LEG can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to achieve expression in the fruit body tissue retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon.

The term "isolated" refers to material, such as a nucleic acid or protein, which is: (1) substantially or essentially free from components which normally accompany or interact with the material as found in its naturally occurring environment, or (2) if the material is in its natural environment, the material has been altered by deliberate human intervention to a composition and/or placed at a locus in a cell other than the locus native to the material. Methods for isolation of promoter regions are well known in the art. One method is the use of primers and genomic DNA used in conjunction with the Genome Walker Kit™ (Clonetech).

The *A. bisporus* lectin promoter is set forth in SEQ ID NO:1, with functional truncations shown in SEQ ID NO:2, SEQ ID NO:3 and SEQ ID NO: 4. The minimal core promoter is 45 nucleotides in length, with the full-length promoter being approximately 135 to 180 nucleotides in length. 160 is 818 base pair nucleotides in length. The lectin promoter was isolated from the *A. bisporus* lectin coding region.

The regulatory regions of the invention may be isolated from any plant animal or fungi, but is preferably filamentous fungi, including, but not limited to the fungi of the genera Flammulina, *Agaricus, Lentinula*, and *Pleurotus*. Promoters isolated from one fungal species can be expected to express in another fungal species.

Regulatory sequences from other fungi may be isolated according to well-known techniques based on their sequence homology to the coding region of the sequences set forth herein. In these techniques, all or part of the known coding sequence is used as a probe that selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Interscience, New York (1995).

Functional variants of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg et al., "Identification of a 49-bp fragment of the HvLTP2 promoter directing aleurone cell specific expression" Gene 341:49-58 (2004). Such fragments should retain promoter activity, particularly the ability to drive expression in the select tissue. Activity can be measured by Northern blot analysis, reporter activity measurements when using transcriptional fusions, and the like. See, for example, Sambrook et al. (1989) Molecular Cloning: A Laboratory Manual (2nd ed. Cold Spring Harbor Laboratory, Cold Spring Harbor, N.Y.).

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) Methods Enzymol. 155:335-350, and Erlich, ed. (1989) PCR Technology (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name EXO-SIZE™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease 111 is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) PCR Protocols, A Guide to Methods and Applications, eds., Academic Press). Primers used in isolating the promoter of the present invention are shown below.

In referring to a terminator sequence is meant a nucleotide sequence that functions as a polyadenylation signal and signals the end of transcription. Functional fragments that retain such activity are within the scope of the invention.

The regulatory elements disclosed in the present invention, as well as variants and fragments thereof, are useful in the genetic manipulation of any fungus when operably linked with an isolated nucleotide sequence of interest whose expression is to be controlled to achieve a desired phenotypic response.

By "operably linked" is intended a functional linkage between a regulatory region and a second sequence, wherein the regulatory sequence initiates and mediates transcription of the DNA sequence corresponding to the second sequence.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994. The term "nucleotide sequence of interest" refers to a nucleic acid molecule (which may also be referred to as a polynucleotide) which can be an RNA molecule as well as DNA molecule, and can be a molecule that encodes for a desired polypeptide or protein, but also may refer to nucleic acid molecules that do not constitute an entire gene, and which do not necessarily encode a polypeptide or protein. For example, when used in a homologous recombination process, the promoter may be placed in a construct with a sequence that targets an area of the chromosome in the fungi but may not encode a protein. If desired, the nucleotide sequence of interest can be optimized for fungi translation by optimizing the codons used for fungi and the sequence around the translational start site for fungi. Sequences resulting in potential mRNA instability can also be avoided.

The regulatory elements of the invention can be operably linked in expression cassettes along with isolated nucleotide sequences of interest for expression in the desired fungi or plant or animal. Such an expression cassette is provided with a plurality of restriction sites for insertion of the nucleotide sequence of interest under the transcriptional control of the regulatory elements. Alternatively, a specific result can be achieved by providing for a reduction of expression of one or more endogenous products, particularly enzymes or cofactors in fungi. This down regulation can be achieved through many different approaches known to one skilled in the art, including antisense, co-suppression, use of hairpin formations, or others, and discussed infra. Importation or exportation of a cofactor also allows for control of composition. It is recognized that the regulatory elements may be used with their native or other coding sequences to increase or decrease expression of an operably linked sequence in the transformed fungi, plant, seed or animal cell.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and other characteristics. Still other categories of transgenes include genes for inducing expression of exogenous products such as enzymes, cofactors, and hormones. Still others include those encoding an antibody, a secondary metabolite, a therapeutic compound, a biological macromolecule, a medical enzyme; or a gene that confers or contributes to a value-added trait. Examples include a secondary metabolite such as lectin, a therapeutic compound such as a vaccine, a biological macromolecule such as an interferon, endostatin or insulin, a medical enzyme such as a thrombolytic or cerebrosidase and a gene that confers resistance to pests, diseases, or herbicides such as a pesticidal compound *Bacillus thuringiensis* protein (Bt toxin).

It is recognized that any nucleotide sequence of interest, including the native coding sequence, can be operably linked to the regulatory elements of the invention and expressed in fungi.

Means for increasing or inhibiting a protein are well known to those skilled in the art and, include, but are not limited to: transgenic expression, antisense suppression, co-suppression, RNA interference, gene activation or suppression using transcription factors and/or repressors; mutagenesis including, but not limited to, transposon tagging; directed and site-specific mutagenesis, chromosome engineering (see Nobrega et. al., Nature 431:988-993(04)), homologous recombination, TILLING (Targeting Induced Local Lesions In Genomes), and biosynthetic competition to manipulate the expression of proteins. Many techniques for gene silencing are well known to one of skill in the art, including but not limited to knock-outs (such as by insertion of a transposable element such as Mu, Vicki Chandler, The *Maize* Handbook ch. 118 (Springer-Verlag 1994) or other genetic elements such as a FRT, Lox or other site specific integration site; RNA interference (Napoli et al. (1990) Plant Cell 2:279-289; U.S. Pat. No. 5,034,323, Sharp (1999) Genes Dev. 13:139-141, Zamore et al. (2000) Cell 101:25-33; and Montgomery et al. (1998) PNAS USA 95:15502-15507); virus-induced gene silencing (Burton et al. (2000) Plant Cell 12:691-705, and Baulcombe (1999) Curr. Op. Plant Bio. 2:109-113); target-RNA-specific ribozymes (Haseloff et al. (1988) Nature 334:585-591); hairpin structures (Smith et al. (2000) Nature 407:319-320; WO 99/53050; and WO 98/53083); MicroRNA (Aukerman & Sakai (2003) Plant Cell 15:2730-2741); ribozymes (Steinecke et al. (1992) EMBO J. 11:1525, and Perriman et al. (1993) Antisense Res. Dev. 3:253); oligonucleotide mediated targeted modification (e.g., WO 03/076574 and WO 99/25853); zinc-finger targeted molecules (e.g., WO 01/52620; WO 03/048345; and WO 00/42219); and other methods or combinations of the above methods known to those of skill in the art.

The nucleotide sequence operably linked to the regulatory elements disclosed herein can be an antisense sequence for a targeted gene. (See, e.g., Sheehy et al. (1988) PNAS USA 85:8805-8809; and U.S. Pat. Nos. 5,107,065; 5,453,566; and 5,759,829). By "antisense DNA nucleotide sequence" is intended a sequence that is in inverse orientation to the 5'-to-3' normal orientation of that nucleotide sequence. When delivered into a cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in fungi.

As noted, other potential approaches to impact expression of proteins in the fungi include traditional co-suppression, that is, inhibition of expression of an endogenous gene through the expression of an identical structural gene or gene fragment introduced through transformation (Goring, D. R., Thomson, L., Rothstein, S. J. 1991. Proc. Natl. Acad. Sci. USA 88:1770-1774 co-suppression; Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12:883-888; and Neuhuber et al. (1994) Mol. Gen. Genet. 244:230-241)). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said fungal cell. (See, U.S. Pat. No. 5,283,184). The endogenous gene targeted for co-suppression may be a gene encoding any protein that accumulates in the fungal species of interest.

Additional methods of down-regulation are known in the art and can be similarly applied to the instant invention. These methods involve the silencing of a targeted gene by spliced hairpin RNA's and similar methods also called RNA interference and promoter silencing (see Smith et al. (2000) Nature 407:319-320, Waterhouse and Helliwell (2003)) Nat. Rev. Genet. 4:29-38; Waterhouse et al. (1998) Proc. Natl. Acad. Sci. USA 95:13959-13964; Chuang and Meyerowitz (2000) Proc. Natl. Acad. Sci. USA 97:4985-4990; Stoutjesdijk et al. (2002) Plant Physiol. 129:1723-1731; and Patent Application WO 99/53050; WO 99/49029; WO 99/61631; WO 00/49035 and U.S. Pat. No. 6,506,559.

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of fungi.

The regulatory region of the invention may also be used in conjunction with another promoter. In one embodiment, the fungal selection marker and the gene of interest can be both functionally linked to the same promoter. In another embodiment, the selection marker and the gene of interest can be functionally linked to different promoters. In yet other embodiments, the expression vector can contain two or more genes of interest that can be linked to the same promoter or different promoters. For example, the SB-LEG promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any compatible promoter. These can be fungal gene promoters, such as, for example, gpd promoter, or promoters from the tumor-inducing plasmids from *Agrobacterium tumefaciens*, such as the nopaline synthase, octopine synthase and mannopine synthase promoters (Velten, J. and Schell, J. (1985) "Selection-expression plasmid vectors for use in genetic transformation of higher plants" Nucleic Acids Res. 13:6981-6998; Depicker et al., (1982) Mol. and Appl. Genet. 1:561-573 Shaw et al. (1984) Nucleic Acids Research vol. 12, No. 20 pp. 7831-7846) that have fungal activity; or viral promoters such as the *Cauliflower mosaic* virus (CaMV) 19S and 35S promoters (Guilley et al. (1982) "Transcription of *Cauliflower mosaic* virus DNA: detection of promoter sequences, and characterization of transcripts" Cell 30:763-773; Odell et al. (1985) "Identification of DNA sequences required for activity of the *cauliflower mosaic* virus 35S promoter" Nature 313:810-812, the figwort mosaic virus FLt promoter (Maiti et al. (1997) "Promoter/leader deletion analysis and plant expression vectors with the figwort mosaic virus (FMV) full length transcript (FLt) promoter containing single or double enhancer domains" Transgenic Res. 6:143-156) or the coat protein promoter of TMV (Grdzelishvili et al., 2000) "Mapping of the *tobacco mosaic* virus movement protein and coat protein subgenomic RNA promoters in vivo" Virology 275: 177-192).

The expression cassette may also include at the 3' terminus of the isolated nucleotide sequence of interest, a transcriptional and translational termination region functional in fungi. The termination region can be native with the promoter nucleotide sequence of the present invention, can be native with the DNA sequence of interest, or can be derived from another source. Thus, any convenient termination regions can be used in conjunction with the promoter of the invention, and are available from the Ti-plasmid of *A. tumefaciens*, such as the octopine synthase and nopaline synthase termination regions. See also: Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

The expression cassettes can additionally contain 5' leader sequences. Such leader sequences can act to enhance translation. Translation leaders are known in the art and include: picomavirus leaders, for example, EMCV leader (Encephalomyocarditis 5' noncoding region), Elroy-Stein et al. (1989) Proc. Natl. Acad. Sci. USA 86:6126-6130; potyvirus leaders, for example, TEV leader (*Tobacco etch* virus), Allison et al. (1986); MDMV leader (*Maize dwarf mosaic* virus), Virology 154:9-20; human immunoglobulin heavy-chain binding protein (BiP), Macejak et al. (1991) Nature 353:90-94; untranslated leader from the coat protein mRNA of Alfalfa mosaic virus (AMV RNA 4), Jobling et al. (1987) Nature 325:622-625); *Tobacco mosaic virus* leader (TMV), Gallie et al. (1989) Molecular Biology of RNA, pages 237-256; and *Maize chlorotic mottle* virus leader (MCMV), Lommel et al. (1991) Virology 81:382-385. See also Della-Cioppa et al. (1987) Plant Physiology 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

Reporter genes can be included in the transformation vectors. Examples of suitable reporter genes known in the art can be found in, for example: Jefferson et al. (1991) in Plant Molecular Biology Manual, ed. Gelvin et al. (Kluwer Academic Publishers), pp. 1-33; DeWet et al. (1987) Mol. Cell. Biol. 7:725-737; Goff et al. (1990) EMBO J. 9:2517-2522; Kain et al. (1995) Bio Techniques 19:650-655; and Chiu et al. (1996) Current Biology 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) EMBO J. 2:987-992; methotrexate, Herrera Estrella et al. (1983) Nature 303:209-213; Meijer et al. (1991) Plant Mol. Biol. 16:807-820; hygromycin, Waldron et al. (1985) Plant Mol. Biol. 5:103-108; Zhijian et al. (1995) Plant Science 108:219-227; streptomycin, Jones et al. (1987) Mol. Gen. Genet. 210:86-91; spectinomycin, Bretagne-Sagnard et al. (1996) Transgenic Res. 5:131-137; bleomycin, Hille et al. (1990) Plant Mol. Biol. 7:171-176; sulfonamide, Guerineau et al. (1990) Plant Mol. Biol. 15:127-136; bromoxynil, Stalker et al. (1988) Science 242:419-423; glyphosate, Shaw et al. (1986) Science 233:478-481; phosphinothricin, DeBlock et al. (1987) EMBO J. 6:2513-2518 including the maize optimized "pat" gene, Gordon-Kamm (1990) The Plant Cell 2: 603; Uchimiya et al. (1993) Bio/Technology 11: 835; and Anzai et al. (1989) Mol. Gen. Gen. 219:492).

Further, when linking a promoter of the invention with a nucleotide sequence encoding a detectable protein, expression of a linked sequence can be tracked in fungi, thereby providing useful screenable or scorable markers. The expression of the linked protein can be detected without the necessity of destroying tissue. By way of example without limitation, the promoter can be linked with detectable markers including a β-glucuronidase, or uidA gene (GUS), which encodes an enzyme for which various chromogenic substrates are known (Jefferson et al., 1986, Proc. Natl. Acad. Sci. USA 83:8447-8451); chloramphenicol acetyl transferase; alkaline phosphatase; a R-locus gene, which encodes a product that regulates the production of anthocyanin pigments (red color) in tissues (Dellaporta et al., in Chromosome Structure and Function, Kluwer Academic Publishers, Appels and Gustafson eds., pp. 263-282 (1988); Ludwig et al. (1990) Science 247:449); a p-lactamase gene (Sutcliffe, Proc. Nat'l. Acad. Sci. U.S.A. 75:3737 (1978)), which encodes an enzyme for which various chromogenic substrates are known (e.g., PADAC, a chromogenic cephalosporin); a xylE gene (Zukowsky et al., Proc. Nat'l. Acad. Sci. U.S.A. 80:1101 (1983)), which encodes a catechol dioxygenase that can convert chromogenic catechols; an α-amylase gene (Ikuta et al., Biotech. 8:241 (1990)); a tyrosinase gene (Katz et al., J. Gen. Microbiol. 129:2703 (1983)), which encodes an enzyme capable of oxidizing tyrosine to DOPA and dopaquinone, which in turn condenses to form the easily detectable compound melanin a green fluorescent protein (GFP) gene (Sheen et al., Plant J. 8(5): 777-84 (1995)); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); DS-RED EXPRESS (Matz et al. (1999) Nature Biotech. 17:969-973, Bevis et al. (2002) Nature Biotech 20:83-87, Haas et al. (1996) Curr. Biol. 6:315-324); *Zoanthus* sp. yellow fluorescent protein (ZsYellow) that has been engineered for brighter fluorescence (Matz et al. (1999) Nature Biotech. 17:969-973, available from BD Biosciences Clontech, Palo Alto, Calif., USA, catalog no. 632443); and cyan florescent protein (CYP) (Bolte et al. (2004) J. Cell Science 117:943-54 and Kato et al. (2002) Plant Physiol 129:913-42).

As noted herein, the present invention provides vectors capable of expressing genes of interest under the control of the regulatory elements. In general, the vectors should be functional in fungal cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra). The transformation vector comprising the regulatory sequence of the present invention operably linked to an isolated nucleotide sequence in an expression cassette, can also contain at least one additional nucleotide sequence for a gene to be co-transformed into the organism. Alternatively, the additional sequence(s) can be provided on another transformation vector. Vectors that are functional in fungi can be binary plasmids derived from *Agrobacterium*. Such vectors are capable of transforming fungal cells. These vectors contain left and right border sequences that are required for integration into the host chromosome. At minimum, between these border sequences is the gene to be expressed under control of the regulatory elements of the present invention. In one embodiment, a selectable marker and a reporter gene are also included.

A transformation vector comprising the particular regulatory sequences of the present invention, operably linked to an isolated nucleotide sequence of interest in an expression cassette, can be used to transform any fungi. In this manner, genetically modified fungi, fungal cells, fungal tissue, and the like can be obtained. Transformation protocols can vary depending on the type of cell. Suitable methods of transforming fungal cells include microinjection, Crossway et al. (1986) Biotechniques 4:320-334; electroporation, Riggs et al. (1986) Proc. Natl. Acad. Sci. USA 83:5602-5606; *Agrobacterium*-mediated transformation, see for example, Townsend et al. U.S. Pat. No. 5,563,055; Romaine et al U.S. Pat. No. 7,700,439, direct gene transfer, Paszkowski et al. (1984) EMBO J. 3:2717-2722; and ballistic particle acceleration, see for example, Sanford et al. U.S. Pat. No. 4,945,050.

The cells that have been transformed can be grown into fungi in accordance with conventional methods. These fungi can then be reproduced with the same transformed strain or different strains. The resulting fungi having constitutive expression of the desired phenotypic characteristic can then be identified. Two or more generations can be grown to ensure that constitutive expression of the desired phenotypic characteristic is stably maintained and inherited.

The following examples are intended to further illustrate the invention and are not to limit the invention in any way. The examples and discussion herein may specifically reference *A. bisporus*, however the teachings herein are equally applicable to any other fungus, preferably filamentous fungi that bear fleshy fruit bodies.

EXAMPLES

Example 1. Identification of a Highly Expressed Lectin Gene Sequence from *Agaricus bisporus*

Using 2-D protein profiling of total soluble protein, a lectin gene was determined to be highly expressed in the fruiting body of *A. bisporus*. Fruiting bodies (commercial intermediate hybrid strain) selected were near maturity, but without exposed gills. Freshly harvested fruit tissue was frozen in liquid nitrogen, pulverized using a mortar and pestle, and extracted with cold acetone with 20% trichloroacetate and 0.2% dithiothreitol and submitted to Alphalyse Inc. (Palo Alto, Calif.) for 2-D protein profiling. The resulting gel image is presented in FIG. 1.

FIG. 1. 2-D Gel Analysis of *Agaricus bisporus* Fruiting Body Proteins.

Protein separation on 2-D SDS PAGE was performed according to the manufacturer's recommendation using IPG drystrips for the first dimension isoelectric focusing, and NuPAGE pre-cast gel system from Invitrogen for the 2nd dimension separation. The numbers identify protein spots excised for MS and MS/MS analysis.

Following electrophoresis, several proteins were identified as highly abundant based on staining intensity on the 2-D gel image. Proteins #4, #6 and #7 (FIG. 1) were among the most abundant and, therefore, were chosen for additional analysis, including peptide mapping and sequencing analysis carried out by Alphalyse Inc. The resulting peptide map and partial peptide sequence information of proteins #4, #6, and #7 were blast searched against a protein database created by Alphalyse Inc. and were shown to match the cDNA sequence of the *A. bisporus* lectin gene (U14936, Crenshaw et al. 1996). The three proteins shared an identical amino acid sequence. The observed separation of the lectin protein into three distinct protein spots probably reflects variation in post-translational modifications, such as glycosylation.

Example 2: Isolation and Sequence Determination of the 5' Upstream DNA Region of the Lectin Gene Encompassing the Promoter The isolation of the genomic 5' upstream DNA region of the lectin gene was carried out using genome walking (APAgene™ Gold Genome Walking Kit, BIO S&T Inc. Montreal, QC, Canada). The following primers: lectin-F1 (5'-TTCGTTCAACGGGACGGAAGAAGCCTTT-3') (SEQ ID NO:5) and lectin-F2 (5'-TCTGGTAGACGC-GAATGCTGATGGTGTA-3') (SEQ ID NO:6) were designed from the lectin cDNA sequence (Crenshaw et al., 1995) and used for genome walking. Genomic DNA of *A. bisporus* was extracted using an AquaGenomic Kit (Multi-Target Pharmaceuticals LLC, Salt Lake City, Utah) and used as the template for genome-walking PCR according to the protocol provided with the APAgene™ Gold Genome Walking Kit. Briefly, four 15-µl aliquots of the PCR reaction mixture were added to PCR tubes labeled A, B, C, and D, using 3× APAgene Gold buffer I for tubes A and B, and APAgene™ Gold buffer II for tubes C and D. The 15 µl of primary PCR mixture contained 5 µl of 3× APAgene™ Gold buffer, 0.3 µl of 50×PCR annealing enhancer, 0.4 µl of 40 mM dNTPs, 0.7 µl of 20 pmol/µl of lectin-F1, 1 µl of genomic DNA (~100 ng), 0.2 µl (1 U) of Taq DNA polymerase (Platinum Taq, Invitrogen, Carlsbad, Calif.) and 7.4 µl of water. The PCR program consisted of one cycle at 94° C. for 4 min followed by 25 cycles at 94° C. for 30 sec, 63° C. for 10 sec, ramp to 66° C. at 0.1° C./sec, and 68° C. for 3 min. and a final cycle at 68° C. for 10 min. Following PCR amplification, 0.3 µl (1.5 U) of Taq polymerase was added to each tube, and 1 µl of 15× degenerate random tagging (DRT) primer A, B, C and D to tube A, B, C and D, respectively. Reaction mixtures were vortexed and subjected to a second PCR program consisting of one cycle at 94° C. for 2 min followed by 1 cycle at 94° C. for 30 sec, 25° C. for 10 sec, ramp to 65° C. at 0.1° C./sec, 68° C. for 6 min, then 20 cycles of 94° C. for 30 sec, 55° C. for 30 sec, 68° C. for 2 min and 50 sec, and a final cycle at 68° C. for 30 min. Following the secondary PCR amplification, 0.5 µl of the PCR product from A, B, C and D tubes was transferred to tubes labeled A1, B1, C1, and D1, respectively. A 1 µl aliquot of 10×DRT primer digestion buffer was added to each tube with 0.5 µl of digestion enzyme mix, and 8 µl of water. The digestion mixtures were vortexed and incubated at 37° C. for 30 min. The enzyme in the digestion mixtures was then heat-inactivated at 95° C. for 5 min. Following the digestion reactions the 5' genomic DNA region upstream of the lectin gene was amplified by nested PCR. For nested PCR, 15 µl of reaction mixture were added to each of four tubes labeled A2, B2, C2, and D2, using 3×APAgene™ Gold buffer I for tubes A2 and B2, and APAgene™ Gold buffer II for tubes C2 and D2. The 15 µl of reaction mixture for the nested PCR contained 5 µl of 3× APAgene™ Gold buffer (I or II), 0.3 µl of 50×PCR annealing enhancer, 0.3 µl of 40 mM dNTPs, 0.4 µl of 20 pmol/µl of lectin-F2 primer, 0.4 µl of Universal Tagging Primer, 0.5 µl of digested PCR product from tubes A1, B1, C1, or D1, and 0.3 µl of Taq DNA polymerase (Invitrogen) and 7.8 µl of water. The nested PCR program for amplification of the putative lectin genes consisted of one cycle at 94° C. for 4 min followed by 30 cycles at 94° C. for 30 sec, 62° C. for 10 sec, ramp to 65° C. at 0.1° C./sec, followed by 68° C. for 2 min and 30 sec and a final cycle at 68° C. for 10 min. PCR products were separated in a 1% agarose gel in 1×TBE (1×TRIS/BORATE/EDTA, 54 g of Tris base, 27.5 g of boric acid, 20 ml of 0.5 M EDTA (pH 8.0) in 1000 ml) by gel electrophoresis. The PCR products of reactions A2, C2 and D2 ranged in size from ~400 bp to ~600 bp. Amplicons were recovered from the agarose gel using a Quick Gel Extraction Kit (Invitrogen).

The PCR amplification products of the putative 5' genomic DNA regions upstream of the lectin genes were cloned into a pCR2.1 TOPO vector using a TOPO TA Cloning Kit (Invitrogen) following the manufacturer's protocol. Briefly, 4 µl of PCR product recovered from the agarose gel was added to 6 µl of pCR2.1 ligation reaction. After ligation for 5 min at room temperature, 3 µl of each reaction mixture were used to transform ONE-SHOT DH5α chemical competent cells (Invitrogen). The transformed cells were plated and selected on LB (Growcells, Irvine, Calif.) agar plate containing 50 µg/ml of kanamycin with 40 µl of 40 mg/ml of X-gal (MP Biomedicals, Solon, Ohio) spread on the surface. After overnight incubation at 37° C. in the dark, white colonies were picked for plasmid DNA preparation. Plasmid DNA was digested with EcoRI and separated by 1% agarose gel electrophoresis in 1×TBE (described above) to identify clones with the correct insert sizes. The clones containing PCR product from the A2 reaction were designated pAGN-743, those from the C2 reaction as pAGN-744 and those from D2 as pAGN-745.

The nucleotide sequence of the lectin gene promoter was determined by sequencing the inserts in pAGN-743, pAGN-744 and pAGN745 using an M13R-reverse primer. Alignment among the insert sequences of pAGN-743, pAGN-744 and pAGN-745 clones revealed that the three PCR products overlapped. pAGN745 clones (pAGN-745-1, -2 and -3) contained the longest 5' genomic DNA region upstream of the lectin gene. The consensus sequence of the 5' genomic DNA region upstream of the lectin gene was generated using sequence information from pAGN-745 clones. The overlap of the consensus sequence with the 5' end cDNA sequence of lectin gene confirmed that the DNA fragment generated by genome walking represented the promoter region of the lectin gene. Alignment between the genomic DNA sequence generated by genome walking and the lectin cDNA sequence (U14936, Crenshaw et al. 1996) revealed an intron in the 5' UTR of lectin mRNA. A nucleotide blast search (blastn) of the consensus sequence of the 5' genomic DNA region upstream of the lectin gene against "all GenBank+EMBL+DDBJ+PDB sequences" failed to show identity with any known sequences, indicating that the isolated sequence was a novel promoter.

Example 3: Demonstrated Ability of the Lectin Promoter to Direct Expression of the GUS Reporter Gene in *Agaricus bisporus*

Figure 2:
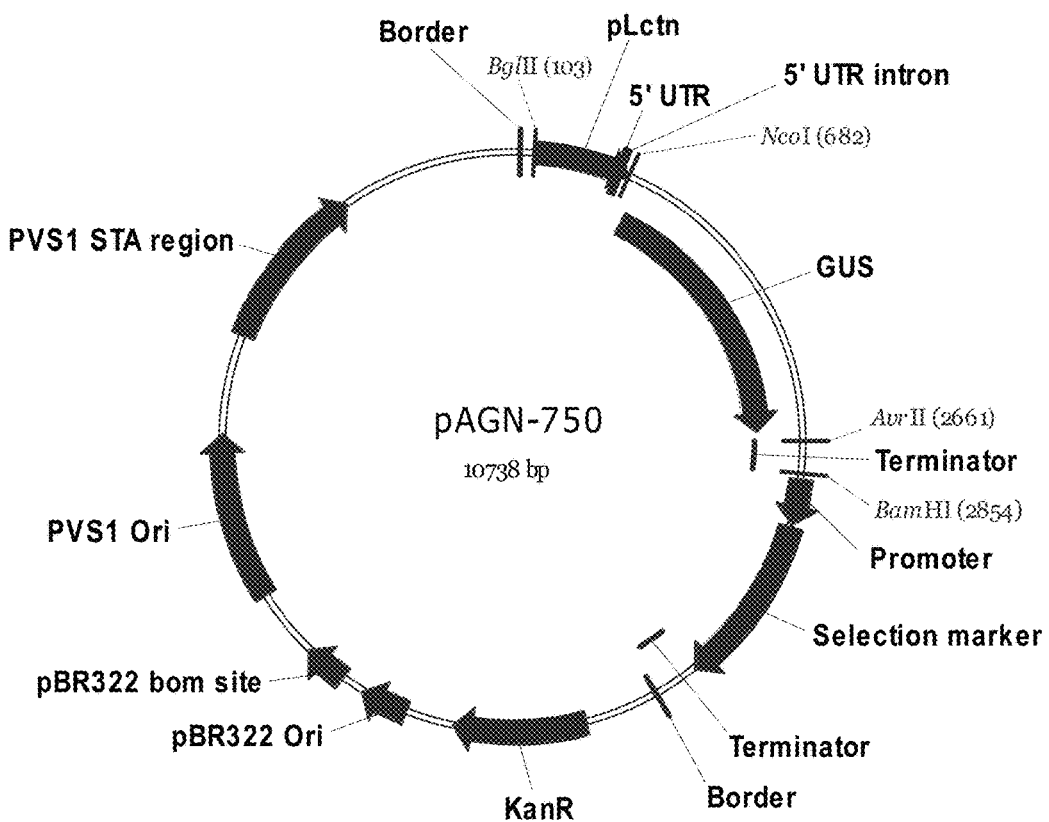
FIG. 2 is a map of binary vector pAGN-750 which includes the promoter of the invention linked to a reporter gene.
Figure 3:
FIG. 3 is a photograph showing expression of a GUS reporter gene in the vegetative mycelium of pAGN-750 events grown on filter paper.

Binary vector pAGN-750 (FIG. 2) was constructed to test the ability of the lectin promoter (designated as pLctn) to drive the expression of a 1-glucuronidase (GUS) reporter gene in *A. bisporus*. pLctn was amplified from pAGN-745 using primers Lctn-BglII (5'-AGCTTAGATCT-GAACACGCG TCGTTTACCTCC-3') (SEQ ID NO:7) and Lctn-NcoI (5'-GTAAGTCCATGGTCTGCTCAACGTTAT-GAG TTAGTTG-3') (SEQ ID NO:8). Restriction enzyme sites, BglII and NcoI, were incorporated into primers to facilitate cloning. The PCR product was digested with BglII/NcoI and the digested product was used to replace the BglII-NcoI fragment in GUS expression vector pAGN-030 to create pAGN-750. The pLctn sequence in pAGN-750 was confirmed by sequencing. pAGN-750 was introduced into *Agrobacterium tumefaciens* and then *A. bisporus* following the transformation procedure described by Chen et al. (2000). Transgenic events generated from pAGN-750 were analyzed for GUS expression (GUS protocol by Sean R. Gallagher, 1991) in the vegetative mycelium and reproductive fruiting body. For determining GUS expression in the mycelium, mycelium of transgenic events was allowed to colonize filter paper for 10-14 days on SM agar plate containing 30 µg/ml of hygromycin B. GUS expression in mycelium was evaluated based on the intensity of blue color present in the mycelial colony exposed to staining buffer on filter paper (FIG. 3). The results of this study showed that pLctn drove GUS expression in the vegetative growth stage of *A. bisporus*. GUS expression in fruit tissue was also evaluated. Mycelia of transgenic events were used to inoculate growth media for mushroom production. Following transformation and selection of transgenic lines on hygromycin, cultures were transferred to liquid media (2% malt extract broth (Difco) and maintained there at room temperature pending inoculation of fruiting media. The liquid media culture was mixed with a sterilized rye/millet grain mixture (50:50) in sterilized 250 ml plastic containers and the transgenic *A. bisporus* mycelia was allowed to colonize the grain substrate for approximately two weeks at room temperature. The fully colonized grain was overlaid with a three cm depth of peat humus casing mixture and the cultures were transferred to 18° C. incubators when mycelium emerged on the top of casing. Cultures were watered frequently to maintain the moist growing environment preferred by the organism. Mature fruit was harvested prior to sporulation and either placed immediately at −80° C. for storage and future analysis or for gus expressing lines, stored briefly at 4° C. prior to analysis by GUS visual staining or the MUG quantitative assay.

For visualization of gus gene expression, 3-mm thick slice from each fruiting body was submerged in GUS staining buffer. GUS expression in fruiting bodies was recorded according to a visual estimation of the intensity of color development in the tissues (Table 1). The findings of this study (Table 1, FIG. 3) showed that pLctn can direct high-level GUS accumulation in the reproductive fruiting body of *A. bisporus*. Variation in the levels of staining intensity among different independent transgenic events was observed for the pAGN-750 construct. This variation can be explained by differences in sequence context resulting from integration of the transgene into different chromosomal locations and/or by differences in transgene copy number between events, which is commonly observed for other promoter/transgene combinations transformed into *A. bisporus* and routinely reported in other plant, animal and fungal systems (Peach C. and Velten J. 1991; Siegal M. L. and Hartl D. L. 1998; Butaye et al. 2005). Fruiting bodies from five events were chosen to quantitatively measure GUS activity using the MUG (4-Methylumbelliferyl glucuronide) assay (Gallagher, S. R. 1991). To extract total soluble protein for the MUG assay, 100 mg of fruiting body tissue were added to a tube containing 300 ul of PBS buffer (IX PBS: 8 g NaCl, 0.2 g KCl, 1.44 g Na$_2$HPO$_4$ and 0.24 g KH$_2$PO$_4$ in 1000 ml, pH 7.4) with 3 glass beads (3.5 mm in diameter) and homogenized at 400 strikes/min for 3 min with Geno/Grinder (SPEX SamplePrep 2000 Geno/Grinder, SPEX SamplePrep LLC, Metuchen, N.J.). Protein concentration in the soluble extract was quantified following the manufacturer's instruction for the BCA Protein Assay Kit (Thermos Scientific, Rockford, Ill.). Quantification of GUS activity in fruiting body tissue is presented as MUG reading per µg of total soluble protein extracted from the tissues. The MUG assay data (Table 2) confirmed the results of the qualitative analysis of GUS expression in the fruiting body. The results are shown in FIG. 3.

TABLE 1

Visual scoring of GUS accumulation in fruiting body tissue

| Event* | Gus Expression Level** | Event | Gus Expression Level** |
|---|---|---|---|
| 750-1A | 0.5 | 750-13A | 2.5 |
| 750-2A | 0.5 | 750-14A | 2.5 |
| 750-3A | 3.5 | 750-15B | 0.5 |
| 750-4A | 2 | 750-16A | 3.5 |
| 750-5A | 2 | 750-17A | 0.5 |
| 750-6A | 1.5 | 750-18B | 2 |
| 750-7A | 3 | 750-19B | 4 |
| 750-8A | 4 | 750-20C | 2 |
| 750-9A | 2.5 | 750-21A | 1.5 |
| 750-10A | 1 | 750-22A | 4 |
| 750-11C | 4 | 750-23A | 1.5 |
| 750-12A | 2.5 | 750-24A | 4 |

*A, B and C represent fruiting body A, B, and C, respectively, of the event
**Fruiting body slices were submerged in GUS staining buffer for 6 hours at RT and the enzyme reaction was stopped by two rinses in water and transfer to a 50% ethanol solution. Rating scale: 1 = pale blue; 2 = moderate blue; 3 = dark blue; 4 = deep dark blue

TABLE 2

Quantitative measurement of GUS activity in the fruiting body.

MUG/Total Protein Ratio for Protein Samples of Whole Fruiting Body Section

| Event ID | 750-3A | 750-8A | 750-16A | 750-19B | 750-22A | Average |
|---|---|---|---|---|---|---|
| Mug reading/ug total protein* | 24.7 | 85.1 | 79.1 | 153.2 | 130.9 | 93.4 |

*MUG reaction was terminated by the addition of 150 ul of NaCO$_2$ after 15 min at 37 C.

Figure 4:
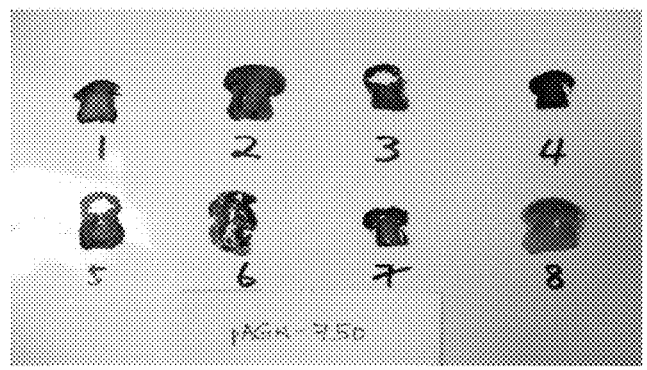
FIG. 4 is a photograph showing GUS staining of fruiting body slices for independent transgenic events of pAGN-750. Sample 1=750-22B; sample 2=750-16A; sample 3=750-6B; sample 4=750-11C; sample 5=750-7A; sample 6=750-13A; sample 7=750-8A; sample 8=750-23A

FIG. 4. GUS staining of fruiting body slices for independent transgenic events of pAGN-750.
Sample 1=750-22B; sample 2=750-16A; sample 3=750-6B; sample 4=750-11C; sample 5=750-7A; sample 6=750-13A; sample 7=750-8A; sample 8=750-23A Example 4: Demonstrated Ability of the Lectin Promoter to Direct Expression of Bovine Trypsin Inhibitor (Aprotinin) in *Agaricus bisporus*

Figure 5:
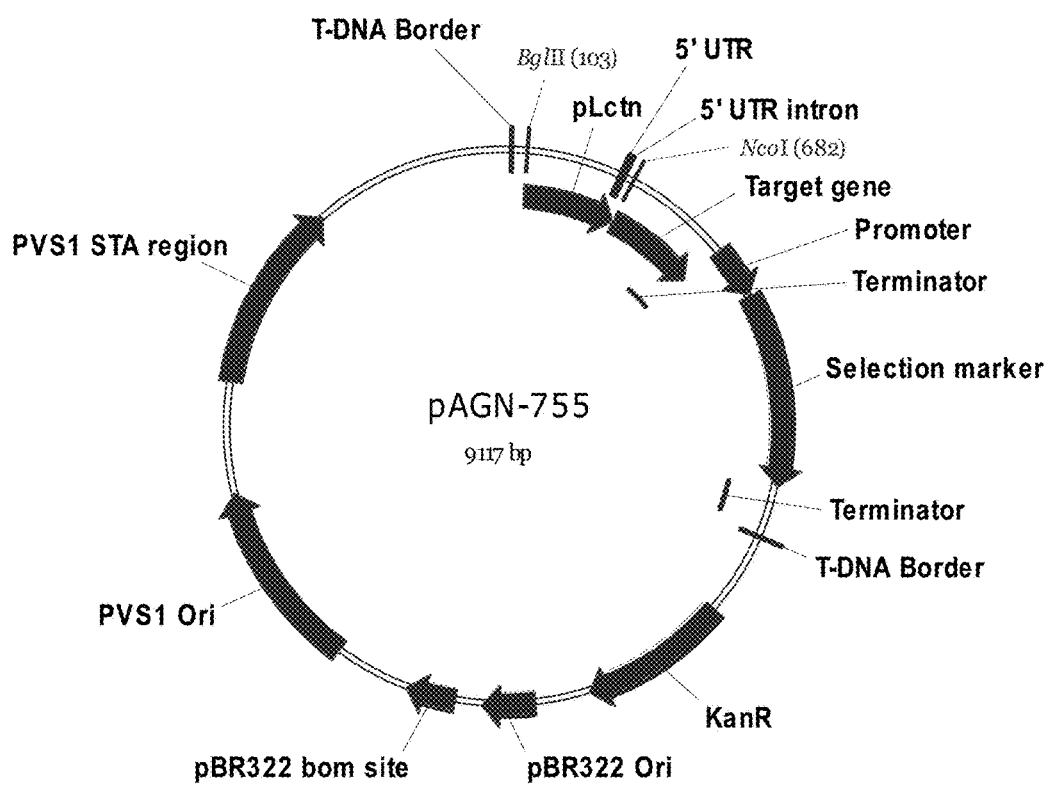
FIG. 5 is a map of Binary vector pAGN-755 which includes the promoter of the invention linked to a target gene of interest.

Binary vector pAGN-755 (FIG. 5) was constructed to test the ability of pLctn to effect expression of an Aprotinin target gene. Construct pAGN-755 was synthesized by replacing the BglII-NcoI promoter fragment in aprotinin expression vector pAGN-021 using the BglII-NcoI-pLctn fragment released from pAGN-750. The pLctn sequence in pAGN-755 was confirmed by sequencing. pAGN-755 was introduced into *A. tumefaciens* and then *A. bisporus* after the transformation procedure described by Chen et al. (2000). Fruiting bodies were produced as described previously for a panel of transgenic events generated using pAGN-755. Aprotinin expression in fruiting body tissue was analyzed using an enzyme-linked immunosorbent assay (ELISA) and Western blotting. High expression of aprotinin, up to 200 mg/kg of fresh fruiting body tissue, was observed (Table 3, FIG. 4).

TABLE 3

Aprotinin expression in pAGN-755 events

| Representative Events | Expression (mg/kg) |
|---|---|
| 755-B10-304 | 14.20 |
| 755-B10-314 | 54.69 |
| 755-B10-325 | 36.40 |
| 755-B10-332 | 35.37 |
| 755-B10-348 | 24.54 |
| 755-B10-352 | 17.27 |
| 755-B10-354 | 15.13 |
| 755-B10-360 | 42.99 |
| 755-B10-363A | 139.65 |
| 755-B10-363B | 205.32 |
| 755-B10-364 | 11.33 |
| 755-B10-380 | 129.22 |
| 755-B10-381 | 22.05 |
| 755-B10-386 | 26.78 |
| 755-B10-388 | 8.21 |
| 755-B10-394 | 18.96 |

Example 5: Determination of the DNA Sequence Essential for Lectin Promoter Activity The minimal region of the 5' genomic DNA region upstream of the lectin gene required for promoter activity was defined by deletion analysis. The following PCR primers were designed and synthesized in order to evaluate the capability of individual segments of this sequence to effect gene expression:

Lctn-BglII-2,
(SEQ ID NO: 9)
5'-AGCTTAGATCTGTCCTGGCACTAGTCACAG-3',

Lctn-BglII-4,
(SEQ ID NO: 10)
5'-AGCTTAGATCTTTGTAGCGCTTGATGC-3',

Lctn-BglII-6,
(SEQ ID NO: 11)
5'-AGCTTAGATCTTATAATTAGCACATACCC-3',

-continued

Lctn-BglII-7,
(SEQ ID NO: 12)
5'-AGCTTAGATCTCGTCTTCATAGATATGGCCAAGCATC-3',

Lctn-BglII-8,
(SEQ ID NO: 13)
5'-AGCTTAGATCTTGCTACTTGTAGATAAGTTTATCTACACC-3',

Lctn-BglII-9,
(SEQ ID NO: 14)
5'-AGCTTAGATCTGATATATAACGATGTCCGATACTTGTG-3',
and

Lctn-BglII-10,
(SEQ ID NO: 15)
5'-AGCTTAGATCTCTTGACTGCGATTCACCTGCTCC-3'.

Primer pairs used for promoter analysis and the expected sizes are listed in Table 4. BglII-NcoI digested PCR products were used to replace the full-length 5' genomic DNA region upstream of the lectin gene in pAGN-774. The resulting vectors were designated pAGN-1279, pAGN-1280, pAGN-1281, pAGN-1282, pAGN-1283, pAGN-1304, and pAGN-1305, as described in Table 4 and FIG. 6.

TABLE 4

Primers and expected promoter size for pLctn deletion analysis

| Primer A | Primer B | Expected Length of Promoter | Vector | Gus Expression |
|---|---|---|---|---|
| Lctn-BglII-2 | Lctn-NcoI | 474 bp | pAGN-1279 | Strong |
| Lctn-BglII-4 | Lctn-NcoI | 369 bp | pAGN-1280 | Strong |
| Lctn-BglII-6 | Lctn-NcoI | 280 bp | pAGN-1281 | Strong |
| Lctn-BglII-7 | Lctn-NcoI | 230 bp | pAGN-1282 | Strong |
| Lctn-BglII-8 | Lctn-NcoI | 180 bp | pAGN-1283 | Strong |
| Lctn-BglII-9 | Lctn-NcoI | 135 bp | pAGN-1304 | Weak |
| Lctn-BglII-10 | Lctn-NcoI | 85 bp | pAGN-1305 | Weak |

FIG. 6 shows the Lectin promoter sequences evaluated. 5' ends DNA sequence in each vector are underlined and the corresponding vector identified. All vectors share the same 3' sequence presented. pAGN-755 and pAGN-750 share the identical sequence.

The constructs incorporating fragments of the 5' region of the lectin gene were transformed into A. tumefaciens and then A. bisporus as described previously. GUS expression driven by the three truncated promoter sequences was compared to that obtained with the full-length 5' genomic DNA region upstream of the lectin gene present in pAGN-774. The sequences are shown in Table 5.

TABLE 5

DNA sequences in each vector used in lectin promoter analysis

| Vectors | Promoter sequence |
|---|---|
| pAGN-750 and pAGN-755 (SEQ ID NO: 16) | GATCTGAACACGCGTCGTTTACCTCCGGGGTGAGTCTCCTGGCACC TTGACAGAATCTAGAATACGATGATCGCACCCTCGATTCCCATGA GCTAAAAATATCTGGTCCTGGCACTAGTCACAGTGGTCACCGACTC GAAAATTTCCCCGTCCATAGTTAACTTTTTTCAACCACAAGTACTC AATCAAATCTACTAGCTTGTAGAAACATTGTAGCGCTTGATGCTGA ATAAATTCAATGCAATCATATAGCATACTACAGATCAACAGGTGC TCAAGCTCAAGCGGGACACTCGATCTATAATTAGCACATACCCCA AAGTGCGGGGGTTAATGGCGCTGGACACTTCGTCTTCATAGATAT GGCCAAGCATCCTTCATGCCATGCTCGAATTATGCTACTTGTAGAT AAGTTTATCTACACCCGCACGGACCAACTAACGTAGATATATAAC GATGTCCGATACTTGTGAATACCTCAGTGGATTATATCCTCTTGAC TGCGATTCACCTGCTCCACTAACACAGTAACCATCTTTCTCTACCA CTGTTTCAACTAACTCATAACGTTGAGCAGACC |
| pAGN-1279 (SEQ ID NO: 17) | GTCCTGGCACTAGTCACAGTGGTCACCGACTCGAAAATTTCCCCGT CCATAGTTAACTTTTTTCAACCACAAGTACTCAATCAAATCTACTA GCTTGTAGAAACATTGTAGCGCTTGATGCTGAATAAATTCAATGCA ATCATATAGCATACTACAGATCAACAGGTGCTCAAGCTCAAGCGG GACACTCGATCTATAATTAGCACATACCCCAAAGTGCGGGGGTTA ATGGCGCTGGACACTTCGTCTTCATAGATATGGCCAAGCATCCTTC ATGCCATGCTCGAATTATGCTACTTGTAGATAAGTTTATCTACACC CGCACGGACCAACTAACGTAGATATATAACGATGTCCGATACTTG TGAATACCTCAGTGGATTATATCCTCTTGACTGCGATTCACCTGCT CCACTAACACAGTAACCATCTTTCTCTACCACTGTTTCAACTAACT CATAACGTTGAGCAGACC |
| pAGN-1280 (SEQ ID NO: 18) | TTGTAGCGCTTGATGCTGAATAAATTCAATGCAATCATATAGCATA CTACAGATCAACAGGTGCTCAAGCTCAAGCGGGACACTCGATCTA TAATTAGCACATACCCCAAAGTGCGGGGGTTAATGGCGCTGGACA CTTCGTCTTCATAGATATGGCCAAGCATCCTTCATGCCATGCTCGA ATTATGCTACTTGTAGATAAGTTTATCTACACCCGCACGGACCAAC TAACGTAGATATATAACGATGTCCGATACTTGTGAATACCTCAGTG GATTATATCCTCTTGACTGCGATTCACCTGCTCCACTAACACAGTA ACCATCTTTCTCTACCACTGTTTCAACTAACTCATAACGTTGAGCA GACC |
| pAGN-1281 (SEQ ID NO: 19) | TATAATTAGCACATACCCCAAAGTGCGGGGGTTAATGGCGCTGGA CACTTCGTCTTCATAGATATGGCCAAGCATCCTTCATGCCATGCTC GAATTATGCTACTTGTAGATAAGTTTATCTACACCCGCACGGACCA ACTAACGTAGATATATAACGATGTCCGATACTTGTGAATACCTCAG TGGATTATATCCTCTTGACTGCGATTCACCTGCTCCACTAACACAG TAACCATCTTTCTCTACCACTGTTTCAACTAACTCATAACGTTGAG CAGACC |

TABLE 5-continued

DNA sequences in each vector used in lectin promoter analysis

| Vectors | Promoter sequence |
|---|---|
| pAGN-1282 (SEQ ID NO: 20) | CGTCTTCATAGATATGGCCAAGCATCCTTCATGCCATGCTCGAATT ATGCTACTTGTAGATAAGTTTATCTACACCCGCACGGACCAACTAA CGTAGATATATAACGATGTCCGATACTTGTGAATACCTCAGTGGAT TATATCCTCTTGACTGCGATTCACCTGCTCCACTAACACAGTAACC ATCTTTCTCTACCACTGTTTCAACTAACTCATAACGTTGAGCAGAC C |
| pAGN-1283 (SEQ ID NO: 21) | TGCTACTTGTAGATAAGTTTATCTACACCCGCACGGACCAACTAAC GTAGATATATAACGATGTCCGATACTTGTGAATACCTCAGTGGATT ATATCCTCTTGACTGCGATTCACCTGCTCCACTAACACAGTAACCA TCTTTCTCTACCACTGTTTCAACTAACTCATAACGTTGAGCAGACC |
| pAGN-1304 (SEQ ID NO: 22) | GATATATAACGATGTCCGATACTTGTGAATACCTCAGTGGATTATA TCCTCTTGACTGCGATTCACCTGCTCCACTAACACAGTAACCATCT TTCTCTACCACTGTTTCAACTAACTCATAACGTTGAGCAGACC |
| pAGN-1305 (SEQ ID NO: 23) | CTTGACTGCGATTCACCTGCTCCACTAACACAGTAACCATCTTTCT CTACCACTGTTTCAACTAACTCATAACGTTGAGCAGACC |

FIG. 7 shows mycelium GUS staining of the events generated from the truncated promoters. Mushroom fruit bodies generated from pAGN-1304 and pAGN-1305 also show very weak or no GUS expression in GUS staining (data not shown).

Data suggested that the minimal full-strength of lectin promoter is between 135 bp to 180 bp, as demonstrated by pAGN-1283, pAGN-1304 and pAGN-1305 GUS expression data.

REFERENCES

Anne-Marie Stomp. Histochemical localization of b-Glucuronidase. pps 103-124 In GUS protocols: using the GUS gene as a reporter of gene expression. 1991 Edited by Sean R. Gallagher.

Chen, X., Stone, M., Schlagnhaufer, C., Romaine, C. P., 2000. A fruiting body tissue method for efficient *Agrobacterium*-mediated transformation of *Agaricus bisporus*. Appl. Environ. Microbiol. 66, 4510-4513.

Crenshaw, R. W., Harper, S. N., Moyer, M. and Privalle, L. S. (1995) Isolation and characterization of a cDNA clone encoding a lectin gene from *Agaricus bisporus*. Plant Physiol. 107(4):1465-1466 (1995).

Rao, G. A. and Flynn, P. Microtiter plate-based assay for b-D-Glucuronidase: a quantitative approach. pp. 89-99. In GUS protocols: using the GUS gene as a reporter of gene expression. 1991 Edited by Sean R. Gallagher.

Peach, C. and Velten, J. (1991) Transgene expression variability (position effect) of CAT and GUS reporter genes driven by linked divergent T-DNA promoters. Plant Molecular Biology vol. 17:49-60.

Butaye, K. M. J., Cammue, B. P. A., Delaure S. L., and De Bolle M. F. C. 2005 Approaches to minimize variation of transgene expression in plants. Molecular Breeding Vol. 16:79-91.

Siegal, M. L. and Hartl, D. L. (1998) An experimental test for lineage-specific position effects on alcohol dehydrogenase (Adh) genes in *Drosophila* Proc. Natl. Acad. Sci. USA Vol. 95, 15513-15518.

Media

| Selection Medium (SM) Agar 500 ml |
|---|
| 10 g malt extract 1.05 g MOPS (or 1.15 MOPS sodium salt) 1.5% agar (7.5 g) Add water to 500 ml pH to 7.0 & BTV Autoclave |

| Selection Medium (SM) 500 ml |
|---|
| 10 g Malt extract 1.05 g MOPS (or 1.15 MOPS sodium salt) 1.5% agar (7.5 g) Add water to 500 ml pH to 7.0 & BTV Autoclave 50 µg/ml Hygromycin B (500 µl of 50 mg/ml) 200 µM Cefotaxim (500 µl of 100 mg/ml) 100 µg/ml Moxalactum (optional) |

| GUS Stain Solution 100 ml |
|---|
| 2 ml 0.5M EDTA (pH 8.0) 1.38 g NaH$_2$PO$_4$ 100 µl Triton X-100 Add water to 100 ml pH to 7.0 with NaOH 0.05 g x-gluc in 2 ml DMF |

What is claimed is:

1. A nucleotide sequence comprising the regulatory element set forth in SEQ ID NO:4 operably linked to a heterologous nucleotide sequence.

2. A fungus stably transformed with nucleotide sequence of claim 1.

3. The fungus of claim 2, wherein said fungus is a filamentous fungus.

4. The fungus of claim 3, wherein said filamentous fungus is an *Agaricus* species.

5. A fruiting body tissue of the fungus of claim 2, wherein the fruiting body tissue comprises the nucleotide sequence.

6. A cell comprising a regulatory element operably linked to a heterologous nucleotide sequence, wherein the regulatory element comprises SEQ ID NO:4.

7. The cell of claim 6 wherein the cell is a plants cell, fungal cell or bacterial cell.

8. A plant comprising the plant cell according to claim 7.

9. A fungus comprising the fungal cell according to claim 7.

10. The fungus of claim 9, wherein said fungus is a filamentous fungus.

11. The fungus of claim 10, wherein said filamentous fungus is an *Agaricus* species.

12. A fruiting body tissue of the fungus of claim 9, wherein the fruiting body tissue comprises the regulatory element operably linked to the heterologous nucleotide sequence.

13. An isolated regulatory element that drives accumulation of either a protein or nucleotide sequence of interest in fruiting body tissue, wherein the regulatory element comprises the nucleotide sequence as set forth in SEQ ID NO:4, and wherein the protein or nucleotide sequence of interest is a heterologous sequence.

* * * * *

SEQUENCE LISTING

<160> NUMBER OF SEQ ID NOS: 23

<210> SEQ ID NO 1
<211> LENGTH: 580
<212> TYPE: DNA
<213> ORGANISM: Agaricus bisporus

<400> SEQUENCE: 1

```
gatctgaaca cgcgtcgttt acctccgggg tgagtctcct ggcaccttga cagaatctag      60
aatacgatga tcgcaccctc gattcccatg agctaaaaat atctggtcct ggcactagtc     120
acagtggtca ccgactcgaa aatttccccg tccatagtta acttttttca accacaagta     180
ctcaatcaaa tctactagct tgtagaaaca ttgtagcgct tgatgctgaa taaattcaat     240
gcaatcatat agcatactac agatcaacag gtgctcaagc tcaagcggga cactcgatct     300
ataattagca catccccaa agtgcggggg ttaatggcgc tggacacttc gtcttcatag      360
atatggccaa gcatccttca tgccatgctc gaattatgct acttgtagat aagtttatct     420
acacccgcac ggaccaacta acgtagatat ataacgatgt ccgatacttg tgaataccct     480
agtggattat atcctcttga ctgcgattca cctgctccac taacacagta accatctttc     540
tctaccactg tttcaactaa ctcataacgt tgagcagacc                           580
```

<210> SEQ ID NO 2
<211> LENGTH: 184
<212> TYPE: DNA
<213> ORGANISM: Agaricus bisporus

<400> SEQUENCE: 2

```
tgctacttgt agataagttt atctacaccc gcacggacca actaacgtag atatataacg      60
atgtccgata cttgtgaata cctcagtgga ttatatcctc ttgactgcga ttcacctgct     120
ccactaacac agtaaccatc tttctctacc actgtttcaa ctaactcata acgttgagca     180
gacc                                                                   184
```

<210> SEQ ID NO 3
<211> LENGTH: 135
<212> TYPE: DNA
<213> ORGANISM: Agaricus bisporus

<400> SEQUENCE: 3

```
gatatataac gatgtccgat acttgtgaat acctcagtgg attatatcct cttgactgcg      60
attcacctgc tccactaaca cagtaaccat ctttctctac cactgtttca actaactcat     120
aacgttgagc agacc                                                       135
```

<210> SEQ ID NO 4
<211> LENGTH: 85
<212> TYPE: DNA
<213> ORGANISM: Agaricus bisporus

<400> SEQUENCE: 4

```
cttgactgcg attcacctgc tccactaaca cagtaaccat ctttctctac cactgtttca      60
actaactcat aacgttgagc agacc                                            85
```

<210> SEQ ID NO 5
<211> LENGTH: 28
<212> TYPE: DNA
<213> ORGANISM: Agaricus bisporus

<400> SEQUENCE: 5
ttcgttcaac gggacggaag aagccttt                                        28

<210> SEQ ID NO 6
<211> LENGTH: 28
<212> TYPE: DNA
<213> ORGANISM: Agaricus bisporus

<400> SEQUENCE: 6
tctggtagac gcgaatgctg atggtgta                                        28

<210> SEQ ID NO 7
<211> LENGTH: 32
<212> TYPE: DNA
<213> ORGANISM: Agaricus bisporus

<400> SEQUENCE: 7
agcttagatc tgaacacgcg tcgtttacct cc                                   32

<210> SEQ ID NO 8
<211> LENGTH: 37
<212> TYPE: DNA
<213> ORGANISM: Agaricus bisporus

<400> SEQUENCE: 8
gtaagtccat ggtctgctca acgttatgag ttagttg                              37

<210> SEQ ID NO 9
<211> LENGTH: 30
<212> TYPE: DNA
<213> ORGANISM: Agaricus bisporus

<400> SEQUENCE: 9
agcttagatc tgtcctggca ctagtcacag                                      30

<210> SEQ ID NO 10
<211> LENGTH: 27
<212> TYPE: DNA
<213> ORGANISM: Agaricus bisporus

<400> SEQUENCE: 10
agcttagatc tttgtagcgc ttgatgc                                         27

<210> SEQ ID NO 11
<211> LENGTH: 29
<212> TYPE: DNA
<213> ORGANISM: Agaricus bisporus

<400> SEQUENCE: 11
agcttagatc ttataattag cacataccc                                       29

<210> SEQ ID NO 12
<211> LENGTH: 37
<212> TYPE: DNA
<213> ORGANISM: Agaricus bisporus

<400> SEQUENCE: 12
agcttagatc tcgtcttcat agatatggcc aagcatc                              37

<210> SEQ ID NO 13
<211> LENGTH: 40
<212> TYPE: DNA
<213> ORGANISM: Agaricus bisporus

<400> SEQUENCE: 13
agcttagatc ttgctacttg tagataagtt tatctacacc                40

<210> SEQ ID NO 14
<211> LENGTH: 38
<212> TYPE: DNA
<213> ORGANISM: Agaricus bisporus

<400> SEQUENCE: 14
agcttagatc tgatatataa cgatgtccga tacttgtg                  38

<210> SEQ ID NO 15
<211> LENGTH: 34
<212> TYPE: DNA
<213> ORGANISM: Agaricus bisporus

<400> SEQUENCE: 15
agcttagatc tcttgactgc gattcacctg ctcc                      34

<210> SEQ ID NO 16
<211> LENGTH: 580
<212> TYPE: DNA
<213> ORGANISM: Agaricus bisporus

<400> SEQUENCE: 16
gatctgaaca cgcgtcgttt acctccgggg tgagtctcct ggcaccttga cagaatctag   60
aatacgatga tcgcaccctc gattcccatg agctaaaaat atctggtcct ggcactagtc  120
acagtggtca ccgactcgaa aatttccccg tccatagtta acttttttca accacaagta  180
ctcaatcaaa tctactagct tgtagaaaca ttgtagcgct tgatgctgaa taaattcaat  240
gcaatcatat agcatactac agatcaacag gtgctcaagc tcaagcggga cactcgatct  300
ataattagca catccccaa gtgcgggggt taatggcgc tggacacttc gtcttcatag   360
atatggccaa gcatccttca tgccatgctc gaattatgct acttgtagat aagtttatct  420
acaccccgcac ggaccaacta acgtagatat ataacgatgt ccgatacttg tgaataccctc  480
agtggattat atcctcttga ctgcgattca cctgctccac taacacagta accatctttc  540
tctaccactg tttcaactaa ctcataacgt tgagcagacc                         580

<210> SEQ ID NO 17
<211> LENGTH: 475
<212> TYPE: DNA
<213> ORGANISM: Agaricus bisporus

<400> SEQUENCE: 17
gtcctggcac tagtcacagt ggtcaccgac tcgaaaattt ccccgtccat agttaacttt   60
tttcaaccac aagtactcaa tcaaatctac tagcttgtag aaacattgta gcgcttgatg  120
ctgaataaat tcaatgcaat catatagcat actacagatc aacaggtgct caagctcaag  180
cgggacactc gatctataat tagcacatac cccaaagtgc ggggttaat ggcgctggac   240
acttcgtctt catagatatg gccaagcatc cttcatgcca tgctcgaatt atgctacttg  300
tagataagtt tatctacacc cgcacggacc aactaacgta gatatataac gatgtccgat  360
acttgtgaat acctcagtgg attatatcct cttgactgcg attcacctgc tccactaaca  420
cagtaaccat ctttctctac cactgtttca actaactcat aacgttgagc agacc       475

<210> SEQ ID NO 18
<211> LENGTH: 370

<212> TYPE: DNA
<213> ORGANISM: Agaricus bisporus

<400> SEQUENCE: 18

| | | | | | |
|---|---|---|---|---|---|
| ttgtagcgct | tgatgctgaa | taaattcaat | gcaatcatat | agcatactac | agatcaacag | 60 |
| gtgctcaagc | tcaagcggga | cactcgatct | ataattagca | catacccaa | agtgcggggg | 120 |
| ttaatggcgc | tggacacttc | gtcttcatag | atatggccaa | gcatccttca | tgccatgctc | 180 |
| gaattatgct | acttgtagat | aagtttatct | acacccgcac | ggaccaacta | acgtagatat | 240 |
| ataacgatgt | ccgatacttg | tgaatacctc | agtggattat | atcctcttga | ctgcgattca | 300 |
| cctgctccac | taacacagta | accatctttc | tctaccactg | tttcaactaa | ctcataacgt | 360 |
| tgagcagacc | | | | | | 370 |

<210> SEQ ID NO 19
<211> LENGTH: 281
<212> TYPE: DNA
<213> ORGANISM: Agaricus bisporus

<400> SEQUENCE: 19

| | | | | | |
|---|---|---|---|---|---|
| tataattagc | acatacccca | aagtgcgggg | gttaatggcg | ctggacactt | cgtcttcata | 60 |
| gatatggcca | agcatccttc | atgccatgct | cgaattatgc | tacttgtaga | taagtttatc | 120 |
| tacacccgca | cggaccaact | aacgtagata | tataacgatg | tccgatactt | gtgaatacct | 180 |
| cagtggatta | tatcctcttg | actgcgattc | acctgctcca | ctaacacagt | aaccatcttt | 240 |
| ctctaccact | gtttcaacta | actcataacg | ttgagcagac | c | | 281 |

<210> SEQ ID NO 20
<211> LENGTH: 231
<212> TYPE: DNA
<213> ORGANISM: Agaricus bisporus

<400> SEQUENCE: 20

| | | | | | |
|---|---|---|---|---|---|
| cgtcttcata | gatatggcca | agcatccttc | atgccatgct | cgaattatgc | tacttgtaga | 60 |
| taagtttatc | tacacccgca | cggaccaact | aacgtagata | tataacgatg | tccgatactt | 120 |
| gtgaatacct | cagtggatta | tatcctcttg | actgcgattc | acctgctcca | ctaacacagt | 180 |
| aaccatcttt | ctctaccact | gtttcaacta | actcataacg | ttgagcagac | c | 231 |

<210> SEQ ID NO 21
<211> LENGTH: 184
<212> TYPE: DNA
<213> ORGANISM: Agaricus bisporus

<400> SEQUENCE: 21

| | | | | | |
|---|---|---|---|---|---|
| tgctacttgt | agataagttt | atctacaccc | gcacggacca | actaacgtag | atatataacg | 60 |
| atgtccgata | cttgtgaata | cctcagtgga | ttatatcctc | ttgactgcga | ttcacctgct | 120 |
| ccactaacac | agtaaccatc | tttctctacc | actgtttcaa | ctaactcata | acgttgagca | 180 |
| gacc | | | | | | 184 |

<210> SEQ ID NO 22
<211> LENGTH: 135
<212> TYPE: DNA
<213> ORGANISM: Agaricus bisporus

<400> SEQUENCE: 22

| | | | | | |
|---|---|---|---|---|---|
| gatatataac | gatgtccgat | acttgtgaat | acctcagtgg | attatatcct | cttgactgcg | 60 |

-continued

```
attcacctgc tccactaaca cagtaaccat ctttctctac cactgtttca actaactcat    120
aacgttgagc agacc                                                     135

<210> SEQ ID NO 23
<211> LENGTH: 85
<212> TYPE: DNA
<213> ORGANISM: Agaricus bisporus

<400> SEQUENCE: 23
cttgactgcg attcacctgc tccactaaca cagtaaccat ctttctctac cactgtttca    60
actaactcat aacgttgagc agacc                                          85
```